(12) United States Patent
Brolaski et al.

(10) Patent No.: US 8,834,694 B2
(45) Date of Patent: Sep. 16, 2014

(54) DRY COMPOSITIONS AND METHODS FOR GEL ELECTROPHORESIS

(75) Inventors: Mark N. Brolaski, Encinitas, CA (US); Vince Moroney, Rancho Santa Fe, CA (US); Suzanne Kennedy, Carlsbad, CA (US)

(73) Assignee: Mo Bio Laboratories, Inc., Carlsbad, CA (US)

( * ) Notice: Subject to any disclaimer, the term of this patent is extended or adjusted under 35 U.S.C. 154(b) by 341 days.

(21) Appl. No.: 12/979,126

(22) Filed: Dec. 27, 2010

(65) Prior Publication Data

US 2012/0160684 A1    Jun. 28, 2012

(51) Int. Cl.
*B29C 35/02* (2006.01)
*G01N 33/559* (2006.01)
*G01N 27/453* (2006.01)

(52) U.S. Cl.
CPC ............ *G01N 33/559* (2013.01); *G01N 27/453* (2013.01)
USPC ........... 204/450; 204/451; 204/452; 204/600; 204/601

(58) Field of Classification Search
CPC .................................. G01N 27/44756–27/453
USPC ................. 204/450–470, 546–550, 600–621, 204/641–645
See application file for complete search history.

(56) References Cited

U.S. PATENT DOCUMENTS

| 5,064,519 A | 11/1991 | Tice, Jr. et al. |
| 5,861,251 A * | 1/1999 | Park et al. .................... 435/6.12 |
| 2002/0004483 A1* | 1/2002 | Nissen et al. .................. 514/12 |
| 2003/0153724 A1* | 8/2003 | Yamamoto et al. .......... 528/354 |
| 2003/0162246 A1* | 8/2003 | Endo et al. .................... 435/68.1 |
| 2006/0099567 A1 | 5/2006 | Muller-Cohn et al. |
| 2006/0213775 A1* | 9/2006 | Ohashi et al. ................. 204/601 |
| 2006/0240423 A1* | 10/2006 | Quaiser et al. .................... 435/6 |
| 2007/0259038 A1* | 11/2007 | Robertson .................... 424/464 |
| 2008/0308422 A1* | 12/2008 | Smith et al. .................. 204/450 |

FOREIGN PATENT DOCUMENTS

KR        2000-0075140        12/2000

OTHER PUBLICATIONS

Boeseken, Adv. Carbohydrate Chem. (1949) 4:189-210.

* cited by examiner

*Primary Examiner* — Bach Dinh
(74) *Attorney, Agent, or Firm* — Morrison & Foerster LLP

(57) ABSTRACT

The invention provides dry compositions for preparing and loading a sample on a gel for electrophoretic separation. The dry compositions preferably include a tracking dye and a sedimenting agent selected from a five-carbon polyol (e.g., ribitol, arabitol, or xylitol), iso-erythritol, maltitol, and saccharine. Methods for making and using, as well as kits comprising the disclosed compositions, are also provided.

31 Claims, 2 Drawing Sheets

DRY COMPOSITIONS AND METHODS FOR GEL ELECTROPHORESIS

FIELD OF THE INVENTION

The present invention generally relates to the field of gel electrophoresis, and in particular to dry compositions for preparing and loading samples on a gel for electrophoretic separation. The invention further relates to methods for making and using, as well as kits comprising the disclosed compositions.

BACKGROUND OF THE INVENTION

Analysis of the molecular weight of nucleic acids is typically performed using a technique called agarose gel electrophoresis (C. F. Simpson, ELECTROPHORETIC TECHNIQUES, Academic Press, New York (1983)). Alternatively, polyacrylamide can be used instead of agarose. The process of agarose gel electrophoresis involves the formation of a solidified agarose slab gel with pre-formed wells on one end for holding solutions containing nucleic acids. The agarose gel is placed into a box with electrodes on each end and submerged in a buffer that allows for the conduction of an electrical current through the agarose which facilitates the migration of the nucleic acids through the matrix. The electrical field applied results in the negatively charged nucleic acid molecules migrating towards the positively charged pole. The movement of nucleic acids through the porous agarose matrix results in the separation of both DNA and RNA based on molecular weight.

In order for a nucleic acid to be resolved in agarose, it must be applied to the well prior to applying the electric current. Because the agarose gel is submerged under a buffer, it is important to hold the nucleic acid in place within the well of the gel. This requires that the nucleic acid must first be mixed with a solution which contains a compound that adds weight to the sample, thereby allowing the nucleic acid to sink to the bottom of the well and avoid diffusion into the buffer. Weight may be provided from a number of suitable high-density compounds including sucrose, trehalose, glycerol, sorbitol, Ficoll™, and other sugars of various molecular weights.

The typical compound used in loading formulations is Ficoll™ because its high density allows for less diffusion of the nucleic acid in the well, thus providing sharper bands in the agarose gel. Ficoll™ also offers the advantage of working well in the two common gel buffers: Tris-Acetate-EDTA (TAE) and Tris Borate-EDTA (TBE), and in addition, may be stored at room temperature without risk of becoming contaminated. Glycerol is also commonly used in loading dyes but is not as versatile. Glycerol may not be used in TBE gels as the interaction with boric acid in the gel running buffer forms negatively charged esters that migrate in the gel and cause smearing of the nucleic acid bands. (J. Böeseken, *Adv. Carbohydrate Chem.*, 4: 189-210 (1949).) It also requires refrigerated storage to prevent microbial contamination, as do sucrose containing loading dyes. A disadvantage of all the current formulas for nucleic acid loading compositions, including the use of Ficoll, is that they must be used in liquid form, thus requiring the use of a separate receptacle for mixing the nucleic acid and the loading composition together.

Another requirement for adding nucleic acids to the agarose gel well is the presence of a tracking dye to allow for visual assurance that the nucleic acid sample settled into the well and to monitor the progress of the nucleic acid as it travels through the gel to ascertain that it is moving in the correct direction. Loading dyes can be negatively charged, neutral, or positively charged. For example, U.S. Pat. No. 5,064,519 describes the use of neutral and positively charged dyes for nucleic acid electrophoresis. A neutral dye would simply stay in the well and not migrate with the nucleic acid, whereas a positively charged dye would run in the opposite orientation of the negatively charged nucleic acid. Commonly employed nucleic acid loading dyes contain slightly negatively charged dyes, such as bromophenol blue and xylene cyanol. These dyes provide the ability to visualize the migration of nucleic acids into the agarose and prevent over-run of nucleic acids.

In the conventional gel loading process, a liquid solution containing a tracking dye and a sedimenting agent is prepared and mixed with a liquid sample containing a macromolecule to be resolved by electrophoresis, e.g., a nucleic acid, a peptide, or a protein. Because the tracking dye and the sedimenting agent significantly increase the volume of the macromolecular sample, the operator must adjust the volume of the pipette before or after mixing to aspirate the entire sample before loading on a gel. When the number of samples is large, this additional step slows down the work flow and creates undesired delays.

Korean patent publication No. KR2000-0075140 by Kang et al. discloses the use of lyophilization (i.e. freeze-drying) to achieve a semi-dried or condensed version of a DNA molecular weight ladder using Ficoll™ or glycerol as the sugar. The problem with using glycerol for this purpose is that glycerol never reaches complete dryness, even with freeze-drying. This leads to an unstable format for transport as a product and produces variable volumes for gel loading. The semi-dried DNA molecular weight ladder disclosed by Kang et al. requires additional colored dye and EDTA for resuspension. In addition, the inventors discovered that the Ficoll™ dried molecular weight ladder appears distorted in TBE gels.

U.S. Pat. No. 5,861,251 discloses the use of lyophilized enzyme mixes containing dyes and sugar alcohols that are rehydrated upon contact with liquids. The dyes and sugar alcohols are provided for sedimentation and stabilization from heat damage. The stabilizer disclosed in U.S. Pat. No. 5,861,251 is glucitol (sorbitol), which the present inventors found to be unsuitable for use in the present invention because sorbitol does not have adequate density for holding nucleic acid in the agarose or acrylamide well under the buffer and cannot provide optimal resolution of nucleic acid bands in TBE gels.

U.S. Patent Pub. No. 2006/099567 discloses the use of trehalose as a sugar that provides stability to nucleic acids during drying. When the present inventors examined trehalose for its ability to be re-solubilized with the addition of nucleic acid in solution, they found that dried trehalose was very difficult to resuspend upon contact with liquid samples.

Accordingly, there is a need to develop a simple dry composition that contains all the components necessary for gel loading (i.e., a tracking dye and a sedimenting agent providing high density) and is easy to solubilize upon contact with a liquid sample. The present invention effectively addresses this need.

SUMMARY OF THE INVENTION

The present invention provides a novel gel loading composition that allows for use in a dry state, application of the composition to any solid surface for drying, and easy resuspension upon contact with an aqueous solution. In addition, this novel composition provides sufficient density to a macromolecular sample for application to an agarose or acrylamide well under buffer, and allows for high resolution in TAE and/or TBE gel electrophoresis.

In a first aspect, the invention provides a dry composition for loading a sample on a gel. The composition comprises a tracking dye and a sedimenting agent selected from the group consisting of a five-carbon polyol, iso-erythritol, maltitol, saccharine, and a combination thereof. In some embodiments, the five-carbon polyol is selected from the group consisting of ribitol, arabitol, xylitol, and a combination thereof. In some embodiments, the sedimenting agent is selected from the group consisting of ribitol, arabitol, iso-erythritol, and a combination thereof. In some embodiments, the five-carbon polyol is ribitol. In some embodiments, the tracking dye is selected from the group consisting of Bromophenol Blue, Xylene Cyanol, Orange G, Cresol Red, and a combination thereof. In some embodiments, the sedimenting agent is ribitol and the tracking dye is Bromophenol Blue.

In a second aspect, the invention provides a method of producing a dry composition for loading a sample on a gel. The method comprises the following steps: contacting a tracking dye solution with a sedimenting agent solution to form a liquid mixture; optionally depositing a predetermined amount of the liquid mixture on a solid surface; and drying the liquid mixture, wherein said sedimenting agent is selected from the group consisting of five-carbon polyol, iso-erythritol, maltitol, and saccharine. In some embodiments, the five-carbon polyol is selected from the group consisting of ribitol, arabitol, xylitol, and a combination thereof. In some embodiments, the sedimenting agent is selected from the group consisting of ribitol, arabitol, iso-erythritol, and a combination thereof. In some embodiments, the five-carbon polyol is ribitol. In some embodiments, the tracking dye is selected from the group consisting of Bromophenol Blue, Xylene Cyanol, Orange G, Cresol Red, and a combination thereof. In some embodiments, the sedimenting agent is ribitol and the tracking dye is Bromophenol Blue. In some embodiments, the drying of the liquid mixture is performed by air drying, vacuum drying, freeze drying, heating, or a combination thereof.

In a third aspect, the invention provides a method of producing a sample for loading on a gel. The method comprises the following steps: providing a dry composition comprising a tracking dye and a sedimenting agent selected from the group consisting of five-carbon polyol, iso-erythritol, maltitol, and saccharine; and contacting said composition with an aqueous solution comprising a biomolecule. In some embodiments, the method further comprises a step of mixing the composition with the aqueous solution. In some embodiments, the biomolecule is selected from a nucleic acid (e.g., DNA or RNA), a peptide, and a protein. In some embodiments, the five-carbon polyol is selected from the group consisting of ribitol, arabitol, xylitol, and a combination thereof. In some embodiments, the sedimenting agent is selected from the group consisting of ribitol, arabitol, iso-erythritol, and a combination thereof. In some embodiments, the five-carbon polyol is ribitol. In some embodiments, the tracking dye is selected from the group consisting of Bromophenol Blue, Xylene Cyanol, Orange G, Cresol Red, and a combination thereof. In some embodiments, the sedimenting agent is ribitol and the tracking dye is Bromophenol Blue.

In a fourth aspect, the invention provides a kit for loading a sample on a gel. The kit comprises a dry composition immobilized on a solid surface, wherein the composition consists essentially of a tracking dye and a sedimenting agent. In some embodiments, the kit comprises an array of the dry composition immobilized on a solid surface (e.g., a multiwell plate). In some embodiments, the sedimenting agent is selected from the group consisting of a five-carbon polyol, iso-erythritol, maltitol, and saccharine. In some embodiments, the five-carbon polyol is selected from the group consisting of ribitol, arabitol, xylitol, and a combination thereof. In some embodiments, the sedimenting agent is selected from the group consisting of ribitol, arabitol, iso-erythritol, and a combination thereof. In some embodiments, the five-carbon polyol is ribitol. In some embodiments, the tracking dye is selected from the group consisting of Bromophenol Blue, Xylene Cyanol, Orange G, Cresol Red, and a combination thereof. In some embodiments, the sedimenting agent is ribitol and the tracking dye is Bromophenol Blue.

DETAILED DESCRIPTION OF THE INVENTION

Terms and Definitions

Figure 1:
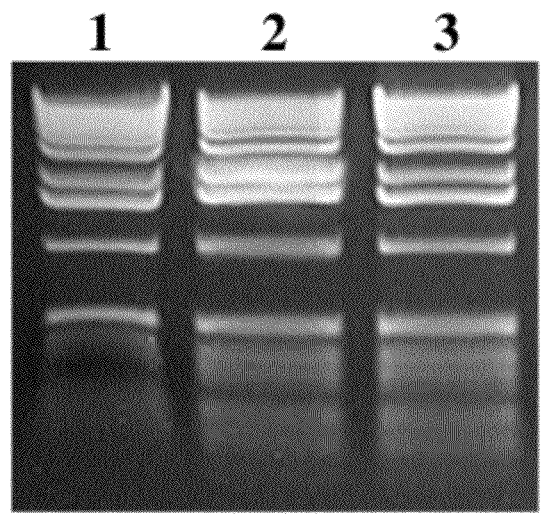
FIG. 1 compares electrophoretic separation of DNA molecular weight ladder samples prepared using Ficoll™ (lane 1, freeze-dried according to Korean patent publication KR2000-0075140), glycerol (lane 2) and ribitol (lane 3) as the sedimenting agents. All three samples were resolved on a TBE agarose gel.

Unless defined otherwise, all technical and scientific terms used herein have the same meaning as is commonly understood by one of ordinary skill in the art to which this invention belongs. All patents, published patent applications, and other publications and databases referred to herein are incorporated by reference in their entireties. If a definition set forth in this section is contrary to or otherwise inconsistent with a definition set forth in patents, published patent applications and other publications and other data bases that are herein incorporated by reference, the definition set forth in this section prevails over the definition that is incorporated herein by reference.

Citation of publications or documents is not intended as an admission that any of such publications or documents are pertinent prior art, nor does it constitute any admission as to the contents or date of these publications or documents.

As used herein, "a" or "an" means "at least one" or "one or more."

Throughout this disclosure, various aspects of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 3, from 2 to 4, from 2 to 5, from 2 to 6, etc., as well as individual numbers within that range, for example, 1, 2, 3, 4, 5 and 6. This applies regardless of the breadth of the range.

Gel Loading Compositions

In a first aspect, the present invention provides a dry composition for loading a sample on a gel in order to carry out electrophoretic separation of one or more macromolecules contained in the sample. The composition includes a tracking dye and a sedimenting agent selected from a five-carbon polyol, iso-erythritol, maltitol, and saccharine. The tracking dye provides a means of following the progress of electrophoresis, whereas the sedimenting agent provides the high density required to sink the sample in a well of the gel and eliminate or at least greatly reduce spillovers.

The five-carbon polyol may be selected from ribitol, arabitol, xylitol, and a combination thereof. In some embodiments, the sedimenting agent is selected from ribitol, arabitol, iso-erythritol, and a combination thereof. In preferred embodiments, the sedimenting agent is the five-carbon polyol ribitol.

The present inventors tested a number of different sugars for their ability to dry at room temperature and resuspend upon contact with liquid with minimal manipulations. The sugars were tested for their ability to provide density to nucleic acid samples in solution and for their ability to produce sharp bands on TAE and TBE agarose gels. Results of these experiments are summarized in Example 2 below. Ficoll™ was found to be resistant to resuspension upon contact with liquid without vigorous mixing. Glycerol was resistant to drying using room temperature air flow. The disaccharide sucrose and monosaccharide glucose required excessive mixing before the sugars would re-dissolve and glucose would not resolve nucleic acid bands with sharp intensity on TBE gels.

In addition, a number of polyols (sugar alcohols) of different molecular sizes were examined for their ability to provide the density and dissolution properties required. Polyols are hydrogenated forms of carbohydrates with carbonyl groups reduced to hydroxyl groups. The six-carbon polyols sorbitol and mannitol demonstrated success in drying but difficulty with dissolution and also did not provide sufficient density to the nucleic acid to hold the sample in the bottom of the agarose well. Moreover, sorbitol appeared to alter the migration of nucleic acids in TBE gels.

The four-carbon polyol iso-erythritol was successful in the drying process, resuspended with good solubility, and provided good resolution of nucleic acids in TAE gels. However, it could not clearly resolve the nucleic acid bands in TBE gels. Similarly, the twelve-carbon polyol maltitol dried well and provided good resolution in TAE gels. However, it was somewhat resistant to resuspension and did not produce required resolution of nucleic acid samples in TBE gels.

Five-carbon polyols demonstrated optimal results in drying and resuspension; however arabitol would not produce optimal nucleic acid resolution in TBE gels, whereas xylitol did not provide optimal density for agarose gel loading and was not optimal for TBE gels. Of the five-carbon polyols tested, ribitol demonstrated the most optimal combination of features. Ribitol provided quick dissolution in liquids, sufficient density for nucleic acid retention in agarose wells, and ideal resolution of nucleic acid bands in TAE and TBE gels.

To the inventors' knowledge, ribitol (also referred to as adonitol) previously has not been used in nucleic acid gel loading compositions and has a number of advantages over the conventionally used sugars that render it optimal for the present invention. First, ribitol can achieve a dried state as a result of room temperature incubation and does not require freeze-drying. Second, unlike most sugars tested, ribitol is easily re-dissolved upon contact with liquid solutions and provides the density needed for complete settling of a nucleic acid sample into the agarose gel well. Finally, in contrast to other sugars tested, ribitol allows for sharp resolution in both TAE and TBE gels.

A variety of tracking dyes can be used in the present gel loading composition, including negatively charged dyes, positively charged dyes, and neutral dyes. The tracking dye may be selected from Bromophenol Blue, Xylene Cyanol, Orange G, Cresol Red, Bromocresol Green, Ethidium Bromide, GelRed®, GelGreen®, Coomassie Brilliant Blue, Brilliant Cresyl Blue, Methylene Blue, Toluidine Blue, Azure A, Patent Blue VF, Acramine Yellow, Sudan III, Alizarin, Alizarine Blue, Alizarine Orange, Gallacetophenone, Hematoxylin, Scarlet Red, Galleon, Blue Dextran; Brilliant Green, Methyl Blue, Methyl Green, Bismark Brown Y, Bismark Brown R, Malachite Green, Neutral Red, Tolonium Chloride, Chrystal Violet, and a combination thereof. In some embodiments, the tracking dye is selected from commonly used tracking dyes such as Bromophenol Blue, Xylene Cyanol, Orange G, Cresol Red, and a combination thereof.

In preferred embodiments, the present gel loading composition includes the five-carbon polyol ribitol as the sedimenting agent and Bromophenol Blue as the tracking dye.

The present composition may further include additional components, such as a buffering agent and/or a chelating agent. The buffering agent may be selected from tris(hydroxymethyl)aminomethane (Tris), phosphate buffered saline (PBS), 3-(N-morpholino)propanesulfonic acid (MOPS), 2-(N-morpholino)ethanesulfonic acid (MES), 4-(2-hydroxyethyl)-1-piperazineethanesulfonic acid (HEPES), and a combination thereof. The chelating agent may be selected from ethylenediaminetetraacetic acid (EDTA), ethylene glycol tetraacetic acid (EGTA), diethylene triamine pentaacetic acid (DTPA), 1,2-bis(o-aminophenoxy)ethane-N,N,N',N'-tetraacetic acid (BAPTA), and a combination thereof. In some embodiments, the composition may also include molecular weight standards, for example, a nucleic acid ladder.

The dry gel loading composition of the present invention may consist essentially of a tracking dye and a sedimenting agent selected from the group consisting of ribitol, arabitol, iso-erythritol, xylitol, maltitol, saccharine, and a combination thereof. In some embodiments, the dry composition includes ribitol as the sedimenting agent and Bromophenol Blue as the tracking dye.

The dry gel loading composition of the present invention may also consist essentially of a tracking dye; a sedimenting agent selected from the group consisting of ribitol, arabitol, iso-erythritol, xylitol, maltitol, saccharine, and a combination thereof; a buffering agent and/or a chelating agent. In some embodiments, the dry composition includes ribitol as the sedimenting agent, Bromophenol Blue as the tracking dye, Tris as the buffering agent, and EDTA as the chelating agent.

It should be appreciated that the present invention contemplates a wide variety of gel loading compositions including many different combinations of the recited tracking dyes and sedimenting agents, even if some of these combinations are not expressly disclosed.

Methods of Manufacture

In a second aspect, the present invention provides a method of making dry gel loading compositions comprising of the following steps: contacting a tracking dye solution with a sedimenting agent solution to form a liquid mixture; optionally depositing a predetermined amount of the liquid mixture on a solid surface; and drying the liquid mixture, wherein the sedimenting agent is selected from a five-carbon polyol, iso-erythritol, maltitol, saccharine, and a combination thereof.

As noted above, the five-carbon polyol may be selected from ribitol, arabitol, xylitol, and a combination thereof. In some embodiments, the sedimenting agent is selected from ribitol, arabitol, iso-erythritol, and a combination thereof. In preferred embodiments, the sedimenting agent is the five-carbon polyol ribitol.

A variety of tracking dyes can be used in the present method, including negatively charged dyes, positively charged dyes, and neutral dyes. The tracking dye may be selected from Bromophenol Blue, Xylene Cyanol, Orange G, Cresol Red, Bromocresol Green, Ethidium Bromide, Gel-Red®, GelGreen®, Coomassie Brilliant Blue, Brilliant Cresyl Blue, Methylene Blue, Toluidine Blue, Azure A, Patent Blue VF, Acramine Yellow, Sudan III, Alizarin, Alizarine Blue, Alizarine Orange, Gallacetophenone, Hematoxylin, Scarlet Red, Galleon, Blue Dextran; Brilliant Green, Methyl Blue, Methyl Green, Bismark Brown Y, Bismark Brown R, Malachite Green, Neutral Red, Tolonium Chloride, Chrystal Violet, and a combination thereof. In some embodiments, the tracking dye is selected from commonly used tracking dyes such as Bromophenol Blue, Xylene Cyanol, Orange G, Cresol Red, and a combination thereof.

In preferred embodiments, the present method utilizes the five-carbon polyol ribitol as the sedimenting agent and Bromophenol Blue as the tracking dye.

The tracking dye concentration in the liquid mixture preferably ranges from about 0.01% to about 0.1%, more preferably from about 0.02% to about 0.06%, and most preferably is about 0.04%. The sedimenting agent concentration in the liquid mixture preferably ranges from about 5% to about 15%, more preferably from about 7.5% to about 12.5%, and most preferably is about 10%. In some embodiments, the liquid mixture formula providing the optimal density with rapid dissolution of the resulting dry composition is about 10% ribitol as the sedimenting agent and about 0.04% Bromophenol Blue as the tracking dye in a buffer or water.

The present method may further comprise a step of contacting the liquid mixture with a solution containing additional components, such as a buffering agent and/or a chelating agent. The buffering agent may be selected from Tris, PBS, MOPS, MES, HEPES, and any combination thereof. The chelating agent may be selected from EDTA, EGTA, DTPA, BAPTA, and any combination thereof. In some embodiments, the liquid mixture may further be contacted with a solution containing a molecular weight standard, such as a nucleic acid molecular weight ladder.

The present method may produce a dry gel loading composition consisting essentially of a tracking dye and a sedimenting agent selected from the group consisting of ribitol, arabitol, iso-erythritol, xylitol, maltitol, saccharine, and a combination thereof. In some embodiments, the dry composition includes ribitol as the sedimenting agent and Bromophenol Blue as the tracking dye.

The present method may also produce a dry gel loading composition consisting essentially of a tracking dye; a sedimenting agent selected from the group consisting of ribitol, arabitol, iso-erythritol, xylitol, maltitol, saccharine, and a combination thereof; a buffering agent and/or a chelating agent. In some embodiments, the dry composition includes ribitol as the sedimenting agent, Bromophenol Blue as the tracking dye, Tris as the buffering agent, and EDTA as the chelating agent.

In the present method, the gel loading composition may be applied to and dried upon a number of solid surfaces, particularly hydrophobic surfaces. The surface can be any form of plastic (e.g., polypropylene, polycarbonate, and other homopolymers or heteropolymers), glass, film (e.g., Parafilm®), or tape. The surface could also be of any shape including a test tube, a multi-well plate, a pipette tip, a capillary, or any other chamber.

The liquid mixture may be dried using air drying, vacuum drying, freeze drying, heating, or any combination of these techniques. In some embodiments, the liquid mixture is dried by air drying at room temperature. In preferred embodiments, approximately 3.0-5.0 µl of the liquid mixture is spotted into individual wells of a Terasaki plate (Greiner Bio-One, Inc.) and allowed to dry overnight at room temperature. The next day, the dried mixture may be used for gel electrophoresis. The composition is not susceptible to contamination, thus allowing for long-term storage at room temperature.

Methods of Use

In a third aspect, the present invention provides a method of producing a sample for loading on a gel. The method comprises the following steps: providing a dry composition comprising a tracking dye and a sedimenting agent selected from the group consisting of a five-carbon polyol, iso-erythritol, maltitol, saccharine, and a combination thereof; and contacting said composition with an aqueous solution. The method may further comprise a step of mixing the dry composition with the aqueous solution, for example, by pipetting up and down, vortexing, or another form of agitation, until the dry composition is fully dissolved and the sample looks homogeneous.

As noted above, the five-carbon polyol may be selected from ribitol, arabitol, xylitol, and a combination thereof. In some embodiments, the sedimenting agent is selected from ribitol, arabitol, iso-erythritol, and a combination thereof. In preferred embodiments, the sedimenting agent is the five-carbon polyol ribitol.

A variety of tracking dyes can be used in the present method, including negatively charged dyes, positively charged dyes, and neutral dyes. The tracking dye may be selected from Bromophenol Blue, Xylene Cyanol, Orange G, Cresol Red, Bromocresol Green, Ethidium Bromide, Gel-Red®, GelGreen®, Coomassie Brilliant Blue, Brilliant Cresyl Blue, Methylene Blue, Toluidine Blue, Azure A, Patent Blue VF, Acramine Yellow, Sudan III, Alizarin, Alizarine Blue, Alizarine Orange, Gallacetophenone, Hematoxylin, Scarlet Red, Galleon, Blue Dextran; Brilliant Green, Methyl Blue, Methyl Green, Bismark Brown Y, Bismark Brown R, Malachite Green, Neutral Red, Tolonium Chloride, Chrystal Violet, and a combination thereof. In some embodiments, the tracking dye is selected from commonly used tracking dyes such as Bromophenol Blue, Xylene Cyanol, Orange G, Cresol Red, and a combination thereof.

In preferred embodiments, the present method utilizes the five-carbon polyol ribitol as the sedimenting agent and Bromophenol Blue as the tracking dye.

The aqueous solution may comprise a macromolecule to be resolved by electrophoresis, such as a nucleic acid (e.g., DNA or RNA), a peptide, or a protein. In some embodiments, the macromolecule comprises a molecular weight standard, such as a nucleic acid molecular weight ladder. The aqueous solution may further comprise additional components, such as a buffering agent and/or a chelating agent. The buffering agent may be selected from Tris, PBS, MOPS, MES, HEPES, and any combination thereof.

In some embodiments, the buffering agent is Tris used at a concentration of approximately 10 mM. The chelating agent may be selected from EDTA, EGTA, DTPA, BAPTA, and any combination thereof. In some embodiments, the chelating agent is EDTA used at a concentration of approximately 1 mM. In some embodiments, the buffering agent is Tris used at a concentration of approximately 10 mM, and the chelating agent is EDTA used at a concentration of approximately 1 mM. Other acceptable concentrations of buffering agents and chelating agents are well known in the art and may also be used with similar effect.

The resuspension volume preferably ranges between 5-20 µl of an aqueous solution for dry compositions ("spots") prepared using 3-5 µl of a liquid mixture containing about 10-20% sedimenting agent and about 0.01-0.1% tracking dye. Larger volumes of an aqueous resuspension solution may be used for larger dry spots. The size of the dry spot may be as large as needed for the desired gel loading volume.

The present method may utilize a dry gel loading composition consisting essentially of a tracking dye and a sedimenting agent selected from the group consisting of ribitol, arabitol, iso-erythritol, xylitol, maltitol, saccharine, and a combination thereof. In some embodiments, the dry composition includes ribitol as the sedimenting agent and Bromophenol Blue as the tracking dye.

The present method may also utilize a dry gel loading composition consisting essentially of a tracking dye; a sedimenting agent selected from the group consisting of ribitol, arabitol, iso-erythritol, xylitol, maltitol, saccharine, and a combination thereof; a buffering agent and/or a chelating agent. In some embodiments, the dry composition includes ribitol as the sedimenting agent, Bromophenol Blue as the tracking dye, Tris as the buffering agent, and EDTA as the chelating agent.

Gel Loading Kits

In a fourth aspect, the invention provides a kit for loading a sample on a gel. The kit comprises a dry composition immobilized on a solid surface, wherein the composition consists essentially of a tracking dye and a sedimenting agent.

As discussed above, the sedimenting agent may be a five-carbon polyol, iso-erythritol, maltitol, saccharine, or a combination thereof. The five-carbon polyol may be selected from ribitol, arabitol, xylitol, and a combination thereof. In some embodiments, the sedimenting agent is selected from ribitol, arabitol, iso-erythritol, and a combination thereof. In preferred embodiments, the sedimenting agent is the five-carbon polyol ribitol.

A variety of tracking dyes can be used in the present kit, including negatively charged dyes, positively charged dyes, and neutral dyes. The tracking dye may be selected from Bromophenol Blue, Xylene Cyanol, Orange G, Cresol Red, Bromocresol Green, Ethidium Bromide, GelRed®, GelGreen®, Coomassie Brilliant Blue, Brilliant Cresyl Blue, Methylene Blue, Toluidine Blue, Azure A, Patent Blue VF, Acramine Yellow, Sudan III, Alizarin, Alizarine Blue, Alizarine Orange, Gallacetophenone, Hematoxylin, Scarlet Red, Galleon, Blue Dextran; Brilliant Green, Methyl Blue, Methyl Green, Bismark Brown Y, Bismark Brown R, Malachite Green, Neutral Red, Tolonium Chloride, Chrystal Violet, and a combination thereof. In some embodiments, the tracking dye is selected from commonly used tracking dyes such as Bromophenol Blue, Xylene Cyanol, Orange G, Cresol Red, and a combination thereof.

In preferred embodiments, the present kit includes the five-carbon polyol ribitol as the sedimenting agent and Bromophenol Blue as the tracking dye.

The present kit may include an array of the dry composition immobilized on a solid surface, for example, a multi-well plate, an array of test tubes, pipette tips or capillaries, plastic, glass, tape, film, or a combination thereof. Where appropriate, the kit may be placed in an air-tight package in order to maintain the activity of any reagents. The package may be, for example, a bag, pouch, or the like fabricated from a material that is substantially non-permeable to moisture. Such materials include, for example, plastic, aluminum foil, and the like. The kit may further include instructions for using the dry gel loading composition of the present invention.

The present inventions will be further described with reference to the following examples; however, it is to be understood that the inventions are not limited to such examples. The following examples are not intended to limit the scope of any claims, but are rather intended to be exemplary of certain embodiments. Any variations in the exemplified methods that occur to the skilled artisan are intended to fall within the scope one or more of the present invention. Parts and percentages are by weight unless otherwise indicated.

EXAMPLES

Example 1

Preparation and Re-Solubilization of Dry Gel Loading Composition

Distilled water (70 ml) was added to a vessel, to which 10 grams of ribitol was added and mixed to dissolve. The solution was brought to a final volume of 100 ml with distilled water and mixed thoroughly, to bring the concentration of ribitol to 10% by weight. Bromophenol Blue was used at a stock concentration of 4%, from which 0.625 ml of the stock was added to the 100 ml ribitol solution. The final concentration of the Bromophenol Blue tracking dye was 0.025% (4%× (0.625 ml/100 ml)=0.025%).

The solution was mixed thoroughly, and approximately 4.5 µl samples of the resulting mixture were spotted into individual wells of a Terasaki plate (Greiner Bio-One, Inc.). The spots were then allowed to dry overnight at room temperature. The following day, the dried spots were ready to be used for agarose gel electrophoresis. The dried composition was not susceptible to contamination, making it suitable for long-term storage at room temperature.

Each spot of the dry gel loading composition prepared as described above was resuspended using 10 µl of an aqueous solution containing about 10 mM Tris, pH 8.0, and optionally containing about 1 mM EDTA. The aqueous solution also contained a DNA molecular weight ladder. Other aqueous solutions were also used with similar results. The dry composition was mixed with the aqueous solution by pipetting the mixture up and down using a 20 µl pipette, until the composition appeared fully dissolved and homogeneous.

Example 2

Performance Comparison of Different Sedimenting Agents

In this study, performance of eleven different sedimenting agents was compared using five distinct parameters: 1) ability to achieve complete dryness at room temperature; 2) ease of dissolution; 3) ability to provide sufficient sample density; 4) quality of separation in a TAE agarose gel; and 5) quality of separation in a TBE agarose gel. The protocols used to prepare and resuspend the dry gel loading compositions were substantially the same as described above in Example 1, with the exception of the different sedimenting agents.

Results of the study are summarized in the table below and in FIGS. 1-4. Referring to the table below, a dissolution speed designated as "1" indicates that 1-5 strokes of a 20 µl pipette was required to solubilize a dry spot in 10 µl of an aqueous solution containing about 10 mM Tris, pH 8.0 and a DNA molecular weight ladder. Dissolution speeds designated as "2," "3" and "4" indicate that the number of strokes required to achieve full solubilization was 5-10, 11-15 and >15, respectively. By way of illustration, Ficoll™ which has a dissolution speed of 4, required 27 pipette strokes to dissolve into solution.

| Type of Sugar | Name | Dries at RT | Dissolution Speed | Provides density | Resolves in TAE | Resolves in TBE |
|---|---|---|---|---|---|---|
| Polysaccharide/epichlorohydrin. | Ficoll | Yes | 4 | Yes | Yes | Yes |
| disaccharide | sucrose | Yes | 3 | Yes | Yes | Yes |
| 12-carbon disaccharide | trehalose | Yes | 3 | Yes | N/A | N/A |
| monosaccharide | dextrose/glucose | Yes | 3 | Yes | Yes | No |
| 3-carbon polyol | glycerol | No | N/A | N/A | N/A | N/A |
| 4-carbon polyol | Iso erythritol | Yes | 1 | marginal | Yes | No |
|  | Arabitol | Yes | 1 | Yes | Yes | No |
| 5-carbon polyol | Xylitol | Yes | 2 | marginal | Yes | No |
|  | Adonitol aka Ribitol | Yes | 1 | Yes | Yes | Yes |
| 6-carbon polyol | sorbitol | Yes | 2 | marginal | Yes | No |
|  | mannitol | Yes | 3 | marginal | N/A | N/A |
| 12-carbon polyol | maltitol | Yes | 2 | Yes | Yes | No |
| polysaccharide of glucose | dextran | Yes | 2 | Yes | No | No |
| 7-carbon sulfilimine | saccharine | Yes | 2 | Yes | Yes | marginal |

As one can see from the table above, each of iso-erythritol, arabitol, xylitol, ribitol, sorbitol, maltitol, dextran and saccharine dried effectively at room temperature and could be solubilized to completion with 10 pipette strokes. In addition, arabitol, ribitol, maltitol, dextran and saccharine provided sufficient density to keep the nucleic acid samples in the agarose gel well and avoid spillovers. Iso-erythritol, xylitol and sorbitol provided marginal sample density. Of the sedimenting agents that performed reasonably well in the first three categories, dextran was the only one that failed to resolve the DNA molecular weight ladder in both TAE and TBE agarose gels. The other sedimenting agents provided good resolution in a TAE agarose gel, and ribitol was the only one that provided excellent resolution in both TAE and TBE agarose gels. Resolutions of the DNA molecular weight ladder obtained in a TBE agarose gel using the different sedimenting agents are compared in FIGS. 1-4.

FIG. 1 compares electrophoretic separation of DNA molecular weight ladder samples prepared using Ficoll™ (lane 1, freeze-dried according to Korean patent publication KR2000-0075140), glycerol (lane 2) and the five-carbon polyol ribitol (lane 3) as the sedimenting agents. As one can see from this figure, the freeze-dried DNA samples prepared with Ficoll™ produced partial band distortion in a TBE agarose gel, particularly in the low molecular weight range. In contrast, the DNA samples prepared with ribitol produced sharp bands with excellent separation.

Figure 2:
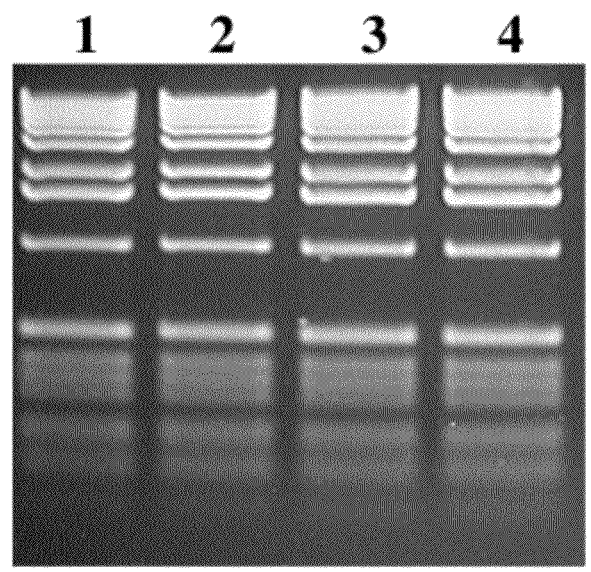
FIG. 2 compares electrophoretic separation of DNA molecular weight ladder samples prepared using Ficoll™ (lanes 1 and 2) and ribitol (lanes 3 and 4) as the sedimenting agents. All four samples were resolved on a TBE agarose gel.

FIG. 2 compares electrophoretic separation of DNA molecular weight ladder samples prepared using Ficoll™ (lanes 1 and 2) and the five-carbon polyol ribitol (lanes 3 and 4) as the sedimenting agents. This figure shows that the DNA samples prepared with Ficoll™ and ribitol using the same protocol produce approximately equal size migration and resolution of the DNA ladder in a TBE agarose gel. However, as noted above, unlike ribitol, Ficoll™ based compositions require significantly more time and effort to achieve complete solubilization in an aqueous solution.

Figure 3:
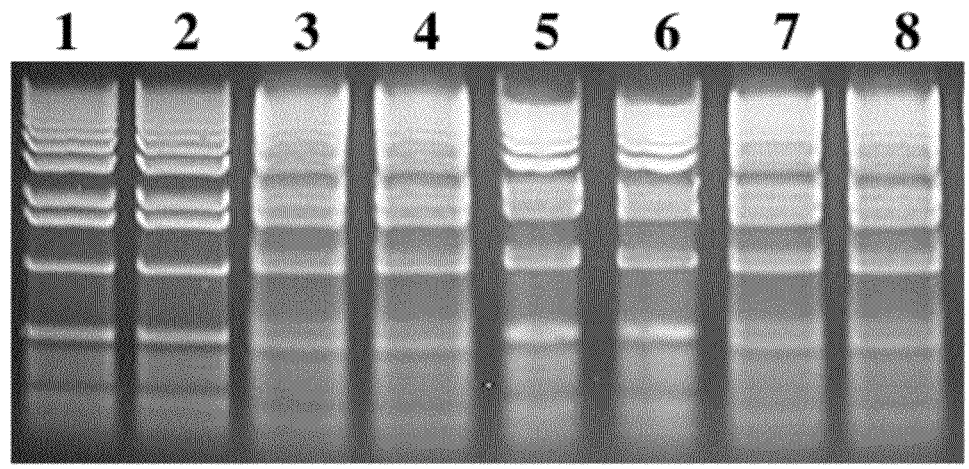
FIG. 3 compares electrophoretic separation of DNA molecular weight ladder samples prepared using ribitol (lanes 1 and 2), arabitol (lanes 3 and 4), iso-erythritol (lanes 5 and 6), and maltitol (lanes 7 and 8) as the sedimenting agents. All eight samples were resolved on a TBE agarose gel.

FIG. 3 compares electrophoretic separation of DNA molecular weight ladder samples prepared using the five-carbon polyols ribitol (lanes 1 and 2) and arabitol (lanes 3 and 4), the four-carbon polyol iso-erythritol (lanes 5 and 6), and the twelve-carbon polyol maltitol (lanes 7 and 8) as the sedimenting agents. This figure clearly shows that ribitol produces superior band separation in a TBE agarose gel and avoids the band distortion problems associated with the other sugars.

Figure 4:
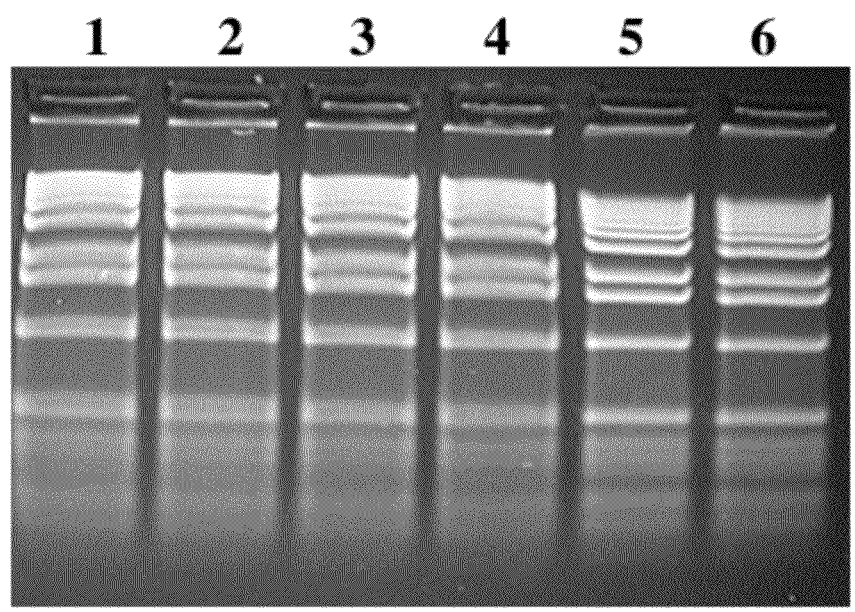
FIG. 4 compares electrophoretic separation of DNA molecular weight ladder samples prepared using sorbitol (lanes 1 and 2), xylitol (lanes 3 and 4), and ribitol (lanes 5 and 6) as the sedimenting agents. All six samples were resolved on a TBE agarose gel.

FIG. 4 compares electrophoretic separation of DNA molecular weight ladder samples prepared using the six-carbon polyol sorbitol (lanes 1 and 2) and the five-carbon polyols xylitol (lanes 3 and 4) and ribitol (lanes 5 and 6) as the sedimenting agents. This figure also clearly demonstrates that ribitol produces superior band separation in a TBE agarose gel and avoids the band distortion problems associated with the other sugars.

The invention claimed is:

1. A dry composition for loading a sample on a gel, said composition comprising a tracking dye and a sedimenting agent, wherein said sedimenting agent is ribitol.

2. The composition of claim 1, wherein the tracking dye is selected from the group consisting of Bromophenol Blue, Xylene Cyanol, Orange G, Cresol Red, Bromocresol Green, Ethidium Bromide, GelRed®, GelGreen®, Coomassie Brilliant Blue, Brilliant Cresyl Blue, Methylene Blue, Toluidine Blue, Azure A, Patent Blue VF, Acramine Yellow, Sudan III, Alizarin, Alizarine Blue, Alizarine Orange, Gallacetophenone, Hematoxylin, Scarlet Red, Galleon, Blue Dextran; Brilliant Green, Methyl Blue, Methyl Green, Bismark Brown Y, Bismark Brown R, Malachite Green, Neutral Red, Tolonium Chloride, Crystal Violet, and a combination thereof.

3. The composition of claim 2, wherein the tracking dye is selected from the group consisting of Bromophenol Blue, Xylene Cyanol, Orange G, Cresol Red, and a combination thereof.

4. The composition of claim 1, wherein the tracking dye is Bromophenol Blue.

5. The composition of claim 1, further comprising a buffering agent and/or a chelating agent.

6. The composition of claim 5, wherein the buffering agent is selected from the group consisting of tris(hydroxymethyl) aminomethane (Tris), phosphate buffered saline (PBS), 3-(N morpholino)propanesulfonic acid (MOPS), 2-(N morpholino)ethanesulfonic acid (MES), 4-(2 hydroxyethyl)-1-piperazineethanesulfonic acid (HEPES), and a combination thereof.

7. The composition of claim 5, wherein the chelating agent is selected from the group consisting of ethylenediaminetetraacetic acid (EDTA), ethylene glycol tetraacetic acid (EGTA), diethylene triamine pentaacetic acid (DTPA), 1,2-bis(o-aminophenoxy)ethane-N,N,N',N'-tetraacetic acid (BAPTA), and a combination thereof.

8. The composition of claim 5, wherein the composition consists essentially of a tracking dye; a sedimenting agent, wherein said sedimenting agent is ribitol; a buffering agent; and a chelating agent.

9. The composition of claim 8, wherein the tracking dye is Bromophenol Blue; the buffering agent is Tris; and the chelating agent is EDTA.

10. The composition of claim 1, wherein the composition consists essentially of a tracking dye and a sedimenting agent; wherein said sedimenting agent is ribitol.

11. The composition of claim 10, wherein the tracking dye is Bromophenol Blue.

12. A method of producing a sample for loading on a gel, said method comprising:
a) providing a dry composition comprising a tracking dye and a sedimenting agent, wherein said sedimenting agent is ribitol and b) contacting said composition with an aqueous solution, thereby producing said sample.

13. The method of claim 12, further comprising mixing said composition with said aqueous solution.

14. The method of claim 12, wherein the aqueous solution comprises a macromolecule selected from a nucleic acid, a peptide, and a protein.

15. The method of claim 14, wherein the nucleic acid is selected from DNA and RNA.

16. The method of claim 12, wherein the tracking dye is selected from the group consisting of Bromophenol Blue, Xylene Cyanol, Orange G, Cresol Red, Bromocresol Green, Ethidium Bromide, GelRed®, GelGreen®, Coomassie Brilliant Blue, Brilliant Cresyl Blue, Methylene Blue, Toluidine Blue, Azure A, Patent Blue VF, Acramine Yellow, Sudan III, Alizarin, Alizarine Blue, Alizarine Orange, Gallacetophenone, Hematoxylin, Scarlet Red, Galleon, Blue Dextran; Brilliant Green, Methyl Blue, Methyl Green, Bismark Brown Y, Bismark Brown R, Malachite Green, Neutral Red, Tolonium Chloride, Crystal Violet, and a combination thereof.

17. The method of claim 16, wherein the tracking dye is selected from the group consisting of Bromophenol Blue, Xylene Cyanol, Orange G, Cresol Red, and a combination thereof.

18. The method of claim 12, wherein the tracking dye is Bromophenol Blue.

19. The method of claim 12, wherein the aqueous solution further comprises a buffering agent and/or a chelating agent.

20. The method of claim 19, wherein the buffering agent is selected from the group consisting of Tris, PBS, MOPS, MES, HEPES, and a combination thereof.

21. The method of claim 19, wherein the chelating agent is selected from the group consisting of EDTA, EGTA, DTPA, BAPTA, and a combination thereof.

22. The method of claim 19, wherein the composition consists essentially of a tracking dye; a sedimenting agent, wherein the sedimenting agent is ribitol; a buffering agent; and a chelating agent.

23. The method of claim 22, wherein the tracking dye is Bromophenol Blue; the buffering agent is Tris; and the chelating agent is EDTA.

24. The method of claim 12, wherein the composition consists essentially of a tracking dye and a sedimenting agent, wherein the sedimenting agent is ribitol.

25. The method of claim 24, wherein the tracking dye is Bromophenol Blue.

26. The method of claim 12, wherein the aqueous solution comprises a buffering agent and/or a chelating agent.

27. The method of claim 26, wherein the buffering agent is selected from the group consisting of Tris, PBS, MOPS, MES, HEPES, and a combination thereof.

28. The method of claim 27, wherein the buffering agent is Tris present at a concentration of approximately 10 mM.

29. The method of claim 26, wherein the chelating agent is selected from the group consisting of EDTA, EGTA, DTPA, BAPTA, and a combination thereof.

30. The method of claim 29, wherein the chelating agent is EDTA present at a concentration of approximately 1 mM.

31. A dry composition for loading a sample on a gel, said composition comprising a tracking dye, which is Bromophenol Blue; a sedimenting agent, which is ribitol; a buffering agent, which is Tris; and a chelating agent, which is EDTA.

* * * * *